United States Patent
Chang et al.

Patent Number: 5,922,729
Date of Patent: Jul. 13, 1999

[54] WATER SOLUBLE POLYMER-TACROLIMUS CONJUGATED COMPOUNDS AND PROCESS FOR PREPARING THE SAME

[75] Inventors: Pan Sup Chang, Guro-ku; Hoon Cho, Chunan-shi, both of Rep. of Korea

[73] Assignee: Kuhnil Pharmaceutical Co., Ltd., Chungnam, Rep. of Korea

[21] Appl. No.: 09/066,818

[22] Filed: Apr. 28, 1998

[30] Foreign Application Priority Data

Jul. 15, 1997 [KR] Rep. of Korea ............ 97-32883

[51] Int. Cl.⁶ ............ A61K 31/395; A61K 31/695; C07D 498/16; C07F 7/04
[52] U.S. Cl. ............ 514/291; 540/456
[58] Field of Search ............ 540/456; 514/291

[56] References Cited

U.S. PATENT DOCUMENTS

| | | | |
|---|---|---|---|
| 4,894,366 | 1/1990 | Okuhara et al. | 514/63 |
| 4,929,611 | 5/1990 | Okuhara et al. | 514/183 |
| 5,164,495 | 11/1992 | Lunetta | 540/456 |
| 5,352,671 | 10/1994 | Baumann et al. | 514/63 |
| 5,532,137 | 7/1996 | Niwa et al. | 435/7.92 |
| 5,624,842 | 4/1997 | Okuhara et al. | 435/253.5 |

OTHER PUBLICATIONS

J. Am. Chem. Soc., 109(16):5031–5032 (1987).

*Primary Examiner*—Mukund J. Shah
*Assistant Examiner*—Bruck Kifle
*Attorney, Agent, or Firm*—Birch, Stewart, Kolasch & Birch, LLP

[57] ABSTRACT

The present invention relates to a tacrolimus conjugated compound represented by formula (I):

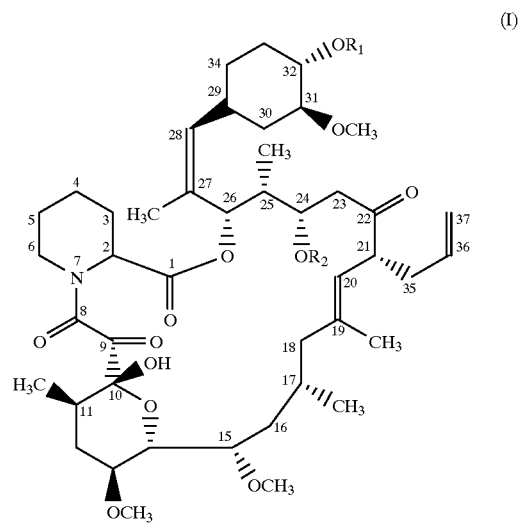

in which $R_1$ and $R_2$ independently of one another represent hydrogen or a group of formula $-CO-CH_2-X-(CH_2CH_2-O)_n-CH_3$ wherein n denotes an integer of 10 to 460, and X represents O or S, provided that both $R_1$ and $R_2$ cannot be hydrogen;

to a process for preparing the same and to its use as an immunosuppressive and antiinflammatory agent.

16 Claims, 2 Drawing Sheets

WATER SOLUBLE POLYMER-TACROLIMUS CONJUGATED COMPOUNDS AND PROCESS FOR PREPARING THE SAME

TECHNICAL FIELD

The present invention relates to a water soluble polymer-tacrolimus conjugate represented by the following formula (I), which is formed by chemically combining tacrolimus to a water soluble polymeric carrier:

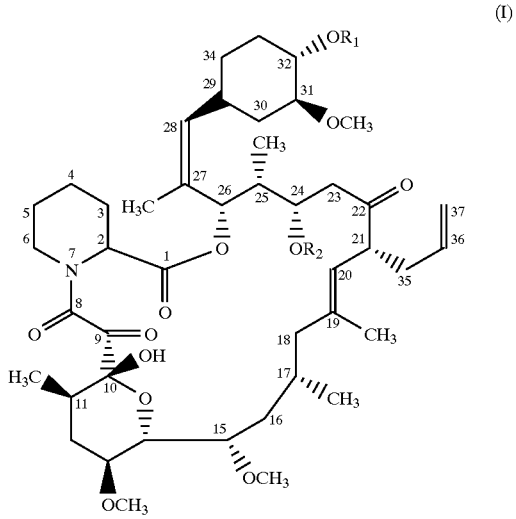

in which $R_1$ and $R_2$ independently of one another represent hydrogen or a group of formula —CO—$CH_2$—X—($CH_2CH_2$—O)n—$CH_3$ wherein n denotes an integer of 10 to 460, and X represents O or S, provided that both $R_1$ and $R_2$ cannot be hydrogen.

More specifically, the present invention relates to a water soluble conjugate of tacrolimus, which exhibits physiological activities of tacrolimus when it is hydrolysed to separate tacrolimus from polymer carrier.

BACKGROUND ART

Tacrolimus is an immunosuppressive agent produced by Streptomyces tsukubaensis No. 9993 and is the compound of formula (I) wherein $R_1$ and $R_2$ are both hydrogen. Tacrolimus, which is also called FK-506, has first discovered by Tanaka, Kuroda and their colleague in Japan [see, J. Am. Chem. Soc., 1987, 109, 5031 and U.S. Pat. No. 4,894,366 issued on Jan. 16, 1990].

Tacrolimus and the related compounds have been shown to be useful in treating obstructive bronchial diseases, particularly asthma, male pattern alopecia, senile alopecia, rheumatoid arthritis, diabetic diseases, posterior uveitisophthalmic diseases, hepatic disorder associated with ischemia, allergic encephalomyelitis, glomerulonephritis, systemic erythematosus lupus, polypharmaceutic resistance, inflammation of mucosal membrane and blood vessel, cytomegaloviral infection and idiopathic thrombocytopenic purpura, hyperthyroidism, etc.

Tacrolimus is combined with intracellular protein FKBP-12 to form a complex of tacrolimus-FKBP-12, Ca, calmodulin and calcineurin, which inhibits phosphate activation of calcineurin and, as a result, inhibits the production of intranuclear factor of activated T cells (NF-AT), which is regarded as a substance initiating genetic transcription for lymphokine (interleukin-2, gamma-interferon) production, to inhibit the activation of T-lymphocytes. Cyclosporin and rapamycin also have been shown to be effective as immunosuppressive agents, and therefore, are useful in preventing transplantation rejection [see, FASEB, 1989, 3, 3411; FASEB, 1989, 3, 5256; Calne, R. et al., Lancet, 1978, 1183; and U.S. Pat. No. 5,180,899].

Tacrolimus is a neutral substance and is generally well dissolved in organic solvents but not in water and n-hexane. Due to such low solubility (12 µg/ml) in water, in formulating the composition castor oil derivatives are required to dissolve tacrolimus. For example, in intravenous injections of tacrolimus 200 mg/ml of hydrogenated polyoxy 60 castor oil (HCO-60) and 80% (v/v) absolute alcohol are required as the solubilizing aid for dissolving 5 mg of tacrolimus.

Substantially no patient who received tacrolimus injection has experienced anaphylaxis. However, other pharmaceutical compositions containing castor oil derivatives have caused anaphylaxis in few patients. Therefore, tacrolimus injection is required for patients who cannot take tacrolimus capsules due to a potential risk of such anaphylaxis. In addition, the use of non-aqueous solvents such as ethanol, propylene glycol or polyethylene glycol 400 in parenteral preparations may cause side effects such as hemolysis, local irritation at injection site, etc., and needs to be carefully considered.

Polyethylene glycol (PEG) is a linear or branched, neutral polymer available in a variety of molecular weights and is well soluble in water and methylene chloride. At molecular weights less than 1000 PEGs are viscous, colorless liquids; and higher molecular weight PEGs are waxy, white solids. The melting point of the solid is proportional to the molecular weight. PEGs having molecular weights ranging from a few hundred to approximately 20,000 are commonly used in biological and biotechnological applications.

Of much interest in the biomedical areas is the fact that polyethylene glycol is nontoxic and was approved by FDA for internal consumption. Polyethylene glycol is very widely used in the field of pharmaceuticals, cosmetics and personal sanitary products. One of the most extensively studied drug delivery systems is the covalent binding of methoxy polyethylene glycol to the surface of protein.

Water soluble polymers such as polyethylene glycol (PEG) and methoxy polyethylene glycol (mPEG) are used for binding the non-aqueous drugs. Therefore, the present invention has developed the novel tacrolimus conjugated compound, which can be dissolved in water, formed by chemically binding the sparingly soluble drug, tacrolimus, with the water soluble polymer, methoxy polyethylene glycol. The conjugated compound of the present invention can be used as an immunosuppressive, antiinflammatory, antifungal, antiproliferative and antitumor agent.

DISCLOSURE OF THE INVENTION

Thus, the present invention relates to a water soluble polymer-tacrolimus conjugated compound represented by the following formula (I), which is formed by chemically combining tacrolimus to a water soluble polymeric carrier:

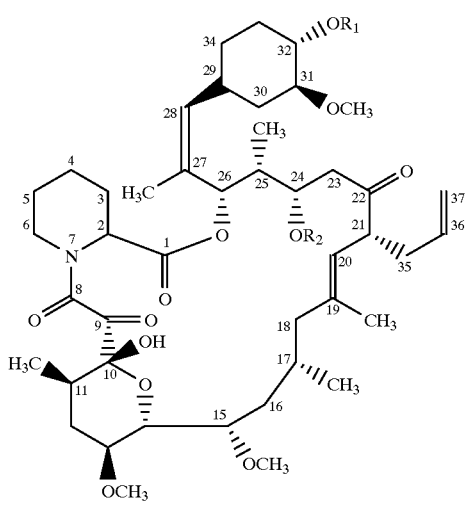

(I)

in which

R₁ and R₂ independently of one another represent hydrogen or a group of formula —CO—CH₂—X—(CH₂CH₂—O)n—CH₃ wherein n denotes an integer of 10 to 460, and X represents O or S, provided that both R₁ and R₂ cannot be hydrogen.

BRIEF DESCRIPTION OF DRAWINGS

For a thorough understanding of the nature and objects of the invention, reference should be made to the following detailed description taken in connection with the accompanying drawings in which.

BEST MODE FOR CARRYING OUT THE INVENTION

As can be seen from the above formula (I), the conjugated compound of the present invention is in the form of an ester wherein the 24- or 32- or 24,32-positions are esterified. The desired 24- or 32- or 24,32-esterified compound of the present invention can be obtained by acylating tacrolimus of formula (II) with an acylating agent of formula (III) at the 24- or 32- or 24,32-positions and then reacting the resulting acylated tacrolimus with a methoxypolyethylene derivative of formula (IV) in the presence of a base such as sodium hydrogen carbonate. The 24-esterified compound, 32-esterified compound and 24,32-diesterified compound can be respectively separated from the mixture by means of chromatography.

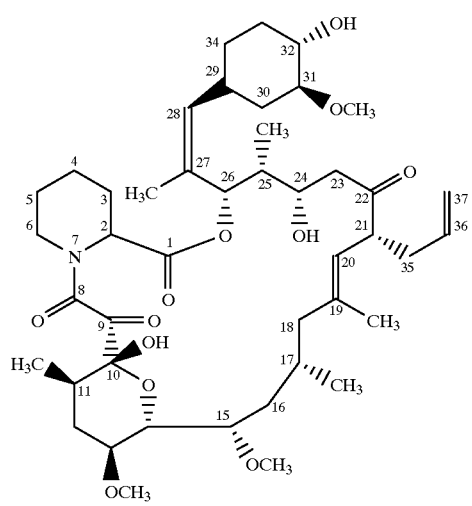

(II)

Y—CH₂—COOH (III)

[HX—(CH₂CH₂O)n—CH₃] (IV)

In the above formulae,

X represents O or S,

Y represents a leaving group such as halogen, and n denotes an integer of 10 to 460, preferably 10 to 140.

To prove that the conjugated compound as synthesized according to the above method is decomposed in the body to produce tacrolimus, the enzyme hydrolysis test is conducted using human liver homogenate at 37° C. Specifically, 2.5 g of human liver is introduced into 2.5 ml of 0.1M phosphate buffer (pH 7.4), homogenized on ice and then centrifuged for 10 minutes. The supernatant is transferred to another test tube. The test solution is prepared by dissolving 7.9 mg (20 mg/ml) of the conjugated compound (tacrolimus 32-methoxypolyethylene glycol-thiol acetate ester) in 0.395 ml of 0.1M phosphate buffer (pH 7.4).

90 μl of the supernatant is introduced into each Eppendorf tube and maintained at 37° C. Then, 10 μl of the test solution which is previously warmed to 30° C. is added thereto. The reaction mixture in each tube is stirred for 5 seconds and 100 μl of acetonitrile is added at the given interval (0, 5, 10, 15, 30, 60, 120 minutes) and then the mixture in the tube is stirred for one minute. The tube is centrifuged at 13,000 rpm for 10 minutes and then stored on ice. In the tube, the final theoretical concentration of the conjugate is 1 mg/ml.

Each 10 μl of the sample solution is analyzed by means of HPLC. For HPLC analysis, a reverse-phase column Inertsil ODS-2 (4.6×150 nm) is used; as the mobile phase gradient solution A (95% water-5% acetonitrile) with 30–80% solution B (95% acetonitrile-5% water) is used; the flow rate is 1.0 ml/min.; and the detector is measured at 214 nm.

Figure 1:
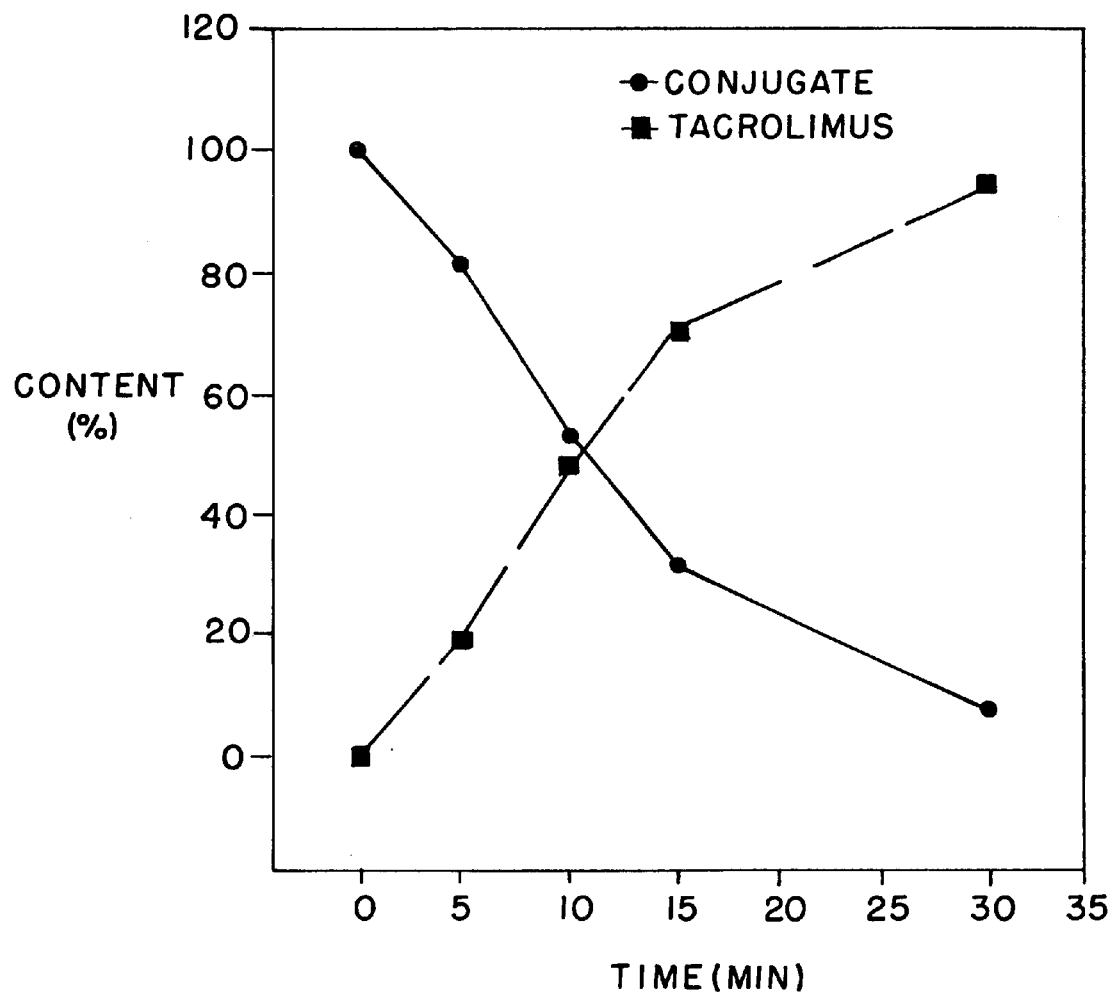
FIG. 1 shows a kinetic profile of the hydrolysis of the conjugated compound of the present invention (tacrolimus 32-methoxypolyethylene glycol 5000-thiol acetate ester) to tacrolimus, as the parent drug, in human liver homogenate at 37° C.
Figure 2:
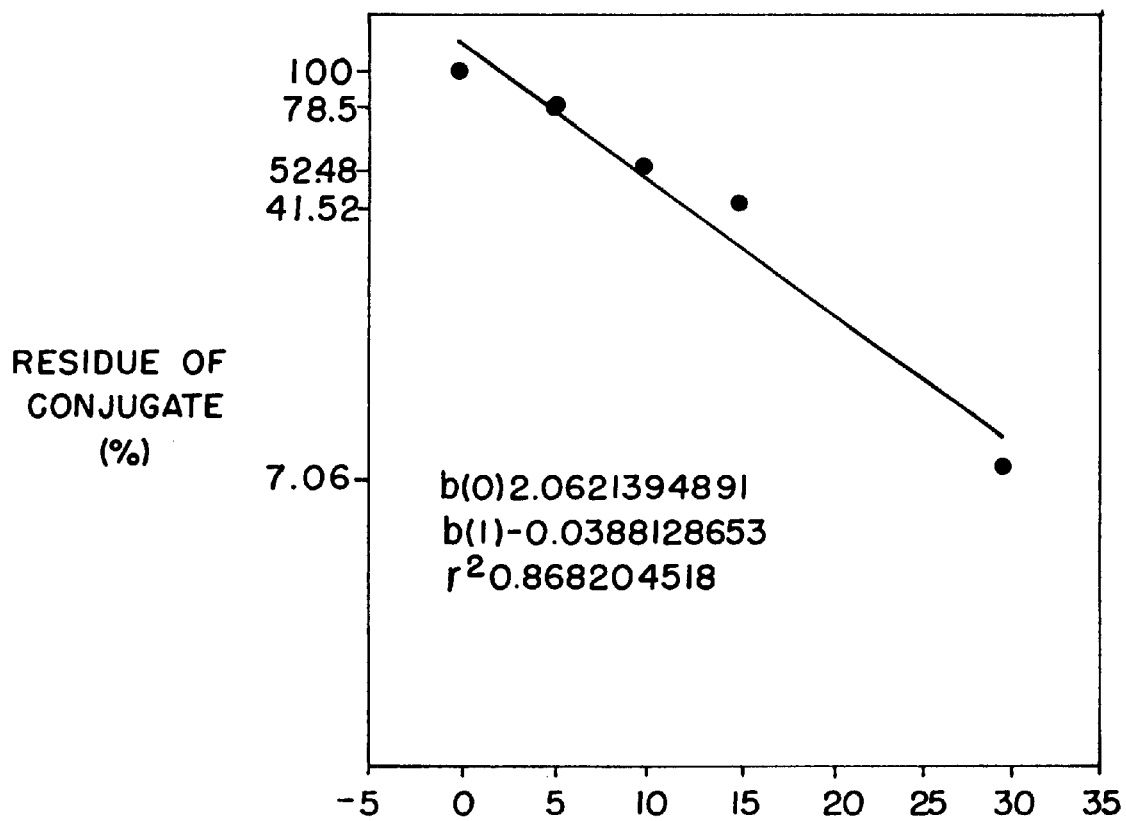
FIG. 2 is a linear graph showing the kinetic profile of the hydrolysis of the conjugated compound of the present invention to tacrolimus in human liver homogenate at 37° C.

As can be seen from FIG. 1, the conjugated compound of the present invention is decomposed in human liver homogenate to produce the active material, tacrolimus. The decomposition of the conjugate is the linear primary reaction as can be seen from FIG. 2. Thus, it can be noted that the conjugate of the present invention is converted again into tacrolimus by the action of enzymes in human liver homogenate, and the hydrolysis half-life of the conjugate is approximately 10 minutes, and 20 hours in phosphate buffer, pH 7.4, at 37° C. This is the ideal for tacrolimus conjugated compound.

In view of the result of enzyme kinetic study, tacrolimus conjugate of the present invention has the same pharmacological usage as tacrolimus itself. That is, the conjugated compound of the present invention can be used in the treatment of transplantation rejection such as kidney, heart, liver, lung, bone marrow, pancreas, cornea, small bowel, and skin allografts, and heart valve xenografts; in the treatment or inhibition of graft vs. host diseases; in the treatment or inhibition of autoimmune diseases such as lupus, rheumatoid arthritis, diabetes mellitus, myasthenia gravis and multiple sclerosis; and in the treatment of inflammation such as psoriasis, dermatitis, eczema, seborrhea, inflammatory bowel disease, pulmonary inflammation (including asthma, chronic obstructive pulmonary disease, emphysema, acute respiratory distress syndrome, bronchitis, and the like) and eye uveitis. In view of the pharmacological activities of tacrolimus, the compounds of the present invention also are considered to have antitumor, antifungal and antiproliferative activities, and therefore, also useful in treating solid tumors, including sarcomas and carcinomas, such as astrocytoma, prostate cancer, breast cancer, lung cancer and ovarian cancer; adult T-cell leukemia/lymphoma; fungal infections; and hyperproliferative vascular diseases such as restenosis and atherosclerosis. When used for restenosis, it is preferred that the compounds of the present invention are used to treat restenosis that occurs following an angioplasty procedure. When used for this purpose, the compounds of the present invention can be administered prior to the procedure, during the procedure, subsequent to the procedure, or any combination of the above.

When administered for the treatment or inhibition of the above disease states, the compounds of the present invention can be administered orally, parenterally, intranasally, intrabronchially, transdermally, topically, intravaginally or rectally. The compounds of the present invention are particularly advantageous as immunosuppressive, antiinflammatory, antifungal, antiproliferative and antitumor agents because of their water solubility.

It is contemplated that when the compounds of the present invention are used as an immunosuppressive or antiinflammatory agent, they can be administered in conjunction with one or more other immunoregulatory agents. Such other immunoregulatory agents include, but are not limited to, azathioprine, corticosteroids, such as prednisolone and methylprednisolone, cyclophosphamide, rapamycin, cyclosporin A, OKT-3, ATG, etc. By combining the compounds of the present invention with such other drugs or agents for inducing immunosuppression or treating inflammatory conditions, the lesser amounts of each of the agents are required to achieve the desired effect.

The compounds of the present invention can be formulated neat or, if necessary, with a pharmaceutical carrier. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which can be mixed with the finely divided active ingredient. In tablets, the active ingredient is mixed with a carrier having the necessary compression properties in suitable proportions and compacted in the shape and size as desired. Suitable solid carriers include, for example, calcium phosphate, magnesium stearate, talc, sugars, lactose, dextrin, starch, gelatin, cellulose, methyl cellulose, sodium carboxymethyl cellulose (sodium CMC), polyvinylpyrrolidone (povidone), low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as buffers, preservatives, sweeteners, flavoring agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, lecithins, and oils (e.g. coconut oil and arachis oil).

For parenteral administration, the carriers are used in sterile liquid form compositions. The liquid carrier for pressurized compositions (in the form of an aerosol) can be halogenated hydrocarbon or other pharmaceutically acceptable propellant. Liquid pharmaceutical compositions which are sterile solutions or suspensions can be utilized by, for example, intramuscular, intraperitoneal or subcutaneous injection. Sterile solutions can also be administered intravenously. The compound of the present invention can also be administered orally either in liquid or solid composition form.

The compounds of the present invention may be administered rectally in the form of a conventional suppository. For administration by intranasal or intrabronchial inhalation or insufflation, the compounds of the present invention may be formulated into an aqueous or partially aqueous solution, which can then be utilized in the form of an aerosol. The compounds of the present invention may also be administered transdermally through the use of a transdermal patch containing the active compound and a carrier that is inert to the active compound of the present invention, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes is composed of absorptive powders dispersed in petroleum or hydrophilic petroleum containing the active ingredient. A variety of occlusive devices may be used to release the active ingredient into the blood stream such as a semipermeable membrane covering a reservoir containing the active ingredient with or without a carrier, or a matrix containing the active ingrdient.

In addition, the compounds of the present invention may be employed as a solution, cream or lotion by formulation with pharmaceutically acceptable vehicles containing 0.1–5%, preferably 2%, of the active compound which may be applied to a fungally affected area.

The dosage requirements vary with the particular compositions employed, the route of administration, the severity of the symptoms presented and the particular subject being treated. Preferably, the pharmaceutical composition is in unit dosage form, e.g. as tablets or capsules. In such form, the composition is sub-divided in unit dose containing appropriate quantities of the active ingredient. The unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The following examples illustrate the preparation of representative compounds of the present invention.

EXAMPLE 1

Synthesis of Tacrolimus Iodoacetate Ester

Tacrolimus (0.3899 g, 0.4743 mmol), dimethylaminopyridine (3 mg, catalytic amount) and iodoacetic acid (0.1097 g, 0.5899 mmol) were dissolved in anhydrous methylene chloride (30 ml). To the resulting solution was slowly added dropwise dicyclohexylcarbodiimide (0.1673 g, 0.8180 mmol)/methylene chloride (15 ml) solution and the mixture was stirred for 4 hours at room temperature. The resulting white precipitate was filtered and the filtrate was evaporated and dried.

Tacrolimus 32-iodoacetate ester, tacrolimus 24-iodoacetate ester and tacrolimus 24,32-diiodoacetate ester as synthesized were isolated respectively by preparative HPLC on Nova-Pack $C_{18}$ column (19×300 mm, 6 micron) eluting with two mobile phases of 5% acetonitrile (solution A) and 95% acetonitrile (solution B) at an appropriate ratio.

1) Tacrolimus 24-iodoacetate Ester

Peak eluted at about 18 minutes was separated and then distilled under reduced pressure to remove the solvent.

MS(FAB) m/z 994(M+Na)$^+$, m/z 972(M+H)$^+$ $^1$H NMR(400 MHz, CDCl$_3$): δ3.642(q, 2H, $C_{24}$—O—CO—CH$_2$—I), 4.90(d, 2H, H-24)

2) Tacrolimus 32-iodoacetate Ester

Peak eluted at about 24.5 minutes was separated and then distilled under reduced pressure to remove the solvent.

MS(FAB) m/z 994(M+Na)$^+$, m/z 972(M+H)$^+$ $^1$H NMR(400 MHz, CDCl$_3$): δ3.70(q, 2H, $C_{32}$—O—CO—CH$_2$—I), 4.71(d, 1H, H-32)

3) Tacrolimus 24,32-diiodoacetate Ester

Peak eluted at about 29 minutes was separated and then distilled under reduced pressure to remove the solvent.

MS(FAB) m/z 1162(M+Na)$^+$ $^1$H NMR(400 MHz, CDCl$_3$): δ3.642(q, 2H, $C_{24}$—O—CO—CH$_2$—I), 3.70(q, 2H, $C_{32}$—O—CO—CH$_2$—I), 4.71(d, 1H, H-32), 4.90(d, 2H, H-24)

EXAMPLE 2

Tacrolimus 24-methoxypolyethylene Glycol 5000 Acetate Ester

Tacrolimus 24-iodoacetate ester (0.09821 g, 0.1194 mmol) was dissolved in 50% acetonitrile-50% sodium hydrogen carbonate (0.1M) solution (100 ml) and then mPEG-SH 5000 (0.7465 g, 0.1493 mmol) was added thereto. The mixture was stirred for 4 hours and extracted with methylene chloride. The methylene chloride layer was dehydrated with anhydrous sodium sulfate and filtered. The filtrate was concentrated to the volume of 5 ml and 250 ml of ether was added thereto to precipitate the product. The precipitated product was filtered to obtain the white amorphous material.

The unreacted methoxypolyethylene glycol was removed by HPLC. According to MS (MALDI/TOF) analysis, the average molecular weight of the product was 5627 and the average molecular weight of mPEG-SH was 4783. The difference in mass (844) exactly matched the tacrolimus acetate moiety.

$^1$H NMR(400 MHz, CDCl$_3$): δ2.85(t, 2H, S—CH$_2$), 3.31 (s, 2H, CO—CH$_2$—s), 3.39(s, 3H, —OCH$_3$), 3.65(m, 4H, —O—CH$_2$—CH$_2$—O), 4.99(m, 1H, H-24)

MS(MALDI/TOF) m/z 5627+—(average molecular weight)

EXAMPLE 3

Tacrolimus 32-methoxypolyethylene Glycol 5000 Acetate Ester

Tacrolimus 32-iodoacetate ester (0.09821 g, 0.1194 mmol) was dissolved in 50% acetonitrile-50% sodium hydrogen carbonate (0.1M) solution (100 ml) and then mPEG-SH 5000 (0.7465 g, 0.1493 mmol) was added thereto. The mixture was stirred for 4 hours and extracted with methylene chloride. The methylene chloride layer was dehydrated with anhydrous sodium sulfate and filtered. The filtrate was concentrated to the volume of 5 ml and 250 ml of ether was added thereto to precipitate the product. The precipitated product was filtered to obtain the white amorphous material.

The unreacted methoxypolyethylene glycol was removed by HPLC. According to MS (MALDI/TOF) analysis, the average molecular weight of the product was 5627 and the average molecular weight of mPEG-SH was 4783. The difference in mass (844) exactly matched the tacrolimus acetate moiety.

$^1$H NMR(400 MHz, CDCl$_3$): δ2.85(t, 2H, S—CH$_2$), 3.34 (s, 2H, CO—CH$_2$—s), 3.38(s, 3H, —OCH$_3$), 3.65(m, 4H, —O—CH$_2$—CH$_2$—O), 4.67(m, 1H, H-32)

MS(MALDI/TOF) m/z 5627+—(average molecular weight)

EXAMPLE 4

Tacrolimus 24,32-di(methoxypolyethylene Glycol 5000 Acetate) Ester

Tacrolimus 24,32-diiodoacetate ester (10 mg, 0.00888 mmol) was dissolved in 50% acetonitrile-50% sodium hydrogen carbonate (0.1M) solution (50 ml) and then mPEG-SH 5000 (0.088 g, 0.01787 mmol) was added thereto. The mixture was stirred for one hour at room temperature and extracted with methylene chloride. The methylene chloride layer was dehydrated with anhydrous sodium sulfate and filtered. The filtrate was concentrated to the volume of 15 ml and ether was added thereto to precipitate the product. The precipitated product was filtered to obtain the white amorphous material.

According to MS (MALDI/TOF) analysis, the average molecular weight of the product was 10667.

$^1$H NMR(400 MHz, CDCl$_3$): δ3.23(q, 2H, $C_{24}$—O—CO—CH$_2$—S—), 3.25(s, $C_{32}$—O—CO—CH$_2$—S—), 4.71 (m, 1H, H-32), 4.92(d, 1H, H-24)

What is claimed is:

1. A compound represented by formula (I):

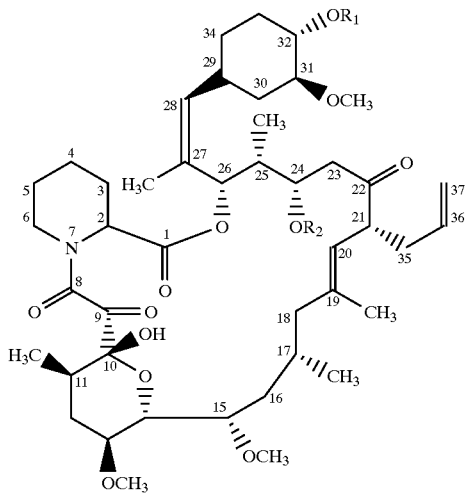

(I)

in which $R_1$ and $R_2$ independently of one another represent hydrogen or a group of formula —CO—CH$_2$—X—(CH$_2$CH$_2$—O)n—CH$_3$ wherein n denotes an integer of 10 to 460, and X represents O or S, provided that both $R_1$ and $R_2$ cannot be hydrogen.

2. The compound according to claim 1, wherein n denotes 10 to 220.

3. The compound according to claim 1, wherein n denotes 10 to 135.

4. The compound according to claim 1, wherein n denotes 10 to 22.

5. The compound according to claim 1, wherein n denotes 90 to 120.

6. The compound according to claim 1, which is an 24-ester with methoxypoly(ethylene glycol)thiol 5000.

7. The compound according to claim 1, which is an 32-ester with methoxypoly(ethylene glycol)thiol 5000.

8. The compound according to claim 1, which is a 24,32-diester with methoxypoly(ethylene glycol)thiol 5000.

9. The compound according to claim 1, which is an 24-ester with methoxypoly(ethylene glycol) 5000.

10. The compound according to claim 1, which is an 32-ester with methoxypoly(ethylene glycol) 5000.

11. The compound according to claim 1, which is a 24,32-diester with methoxypoly(ethylene glycol) 5000.

12. A process for preparing a compound represented by formula (I):

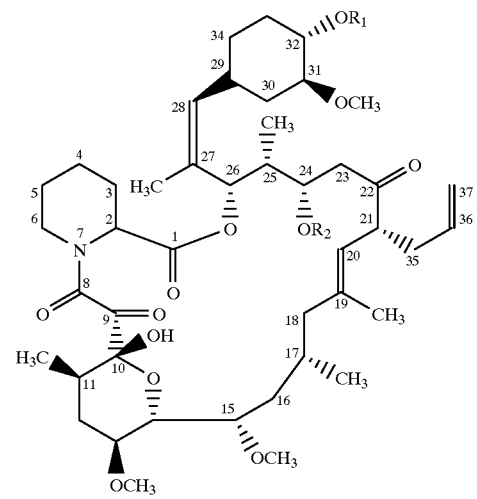

(I)

in which $R_1$ and $R_2$ independently of one another represent hydrogen or a group of formula —CO—CH$_2$—X—(CH$_2$CH$_2$—O)n—CH$_3$ wherein n denotes an integer of 10 to 460, and X represents O or S, provided that both $R_1$ and $R_2$ cannot be hydrogen, which comprises reacting tacrolimus of formula (II):

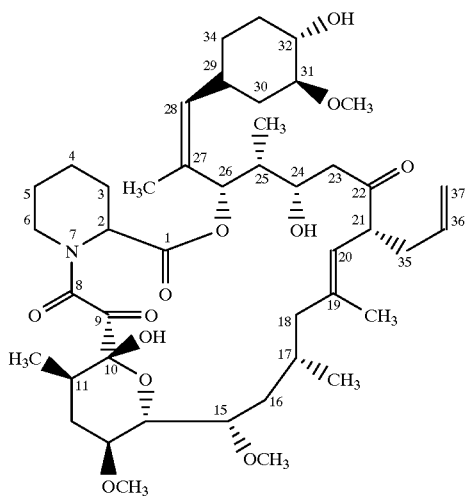

(II)

with an acylating agent of formula (III):

Y—CH$_2$—COOH    (III)

wherein Y represents a leaving group, and then reacting the resulting acylated tacrolimus derivative with a methoxypolyethylene derivative of formula (IV):

$$[HX-(CH_2CH_2O)n-CH_3] \quad (IV)$$

wherein X and n are defined as above, in the presence of a base.

13. The process according to claim 12, wherein the base is sodium hydrogen carbonate.

14. The process according to claim 12, wherein Y represents halogen.

15. A composition which comprises as the active ingredient the compound of formula (I) as defined in claim 1.

16. The process according to claim 13, wherein Y represents halogen.

* * * * *